US010575711B2

(12) United States Patent
Narasawa et al.

(10) Patent No.: US 10,575,711 B2
(45) Date of Patent: Mar. 3, 2020

(54) ENDOSCOPIC SYSTEM

(71) Applicant: OLYMPUS CORPORATION, Hachioji-shi, Tokyo (JP)

(72) Inventors: Takahiro Narasawa, Tokyo (JP); Akihiro Ukai, Tokyo (JP); Yasuhisa Seki, Tokyo (JP); Masanao Hara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/626,724

(22) Filed: Jun. 19, 2017

(65) Prior Publication Data

US 2017/0280968 A1 Oct. 5, 2017

Related U.S. Application Data

(63) Continuation of application No. PCT/JP2015/086094, filed on Dec. 24, 2015.

(30) Foreign Application Priority Data

Dec. 26, 2014 (JP) ................................. 2014-263961

(51) Int. Cl.
*A61B 1/045* (2006.01)
*A61B 1/00* (2006.01)
*H04N 21/436* (2011.01)

(52) U.S. Cl.
CPC ...... *A61B 1/00006* (2013.01); *A61B 1/00009* (2013.01); *A61B 1/00011* (2013.01);
(Continued)

(58) Field of Classification Search
CPC ............ A61B 1/00006; A61B 1/00009; A61B 1/00011; A61B 1/00039; A61B 1/045; H04N 21/436; G06F 3/1204; G06F 3/1254
See application file for complete search history.

(56) References Cited

U.S. PATENT DOCUMENTS 6,195,363 B1 2/2001 Nakatsugawa
2006/0038882 A1 2/2006 Enomoto
(Continued)

FOREIGN PATENT DOCUMENTS

JP H11-004238 A 1/1999
JP 2005-021392 A 1/2005
(Continued)

OTHER PUBLICATIONS

Jun. 5, 2018 Office Action issued in Chinese Patent Application No. 201580070092.3.
(Continued)

*Primary Examiner* — Obafemi O Sosanya
(74) *Attorney, Agent, or Firm* — Oliff PLC

(57) ABSTRACT

Destination management processing units (13,23) of a video processor and a peripheral device each perform destination management processing in a communication between the video processor and the peripheral device. A plurality of communication processing units are situated above the destination management processing unit, respectively correspond to functions of a plurality of peripheral devices, and each process a command. When the destination management processing unit transmits a command, the destination management processing unit adds, to the command to be transmitted, destination information that indicates which of the plurality of communication processing units is to be used. When the destination management processing unit has received a command, the destination management processing unit determines a destination of the received command using destination information added to the received command and distributes the received command to a communication processing unit from among the plurality of communication processing units that is indicated by the destination.

4 Claims, 6 Drawing Sheets

(52) U.S. Cl.
CPC .......... *A61B 1/00039* (2013.01); *A61B 1/045* (2013.01); *H04N 21/436* (2013.01)

(56) References Cited

U.S. PATENT DOCUMENTS

| 2008/0178200 | A1* | 7/2008 | Kaneko | G06F 3/1204 |
| | | | | 719/321 |
| 2009/0216921 | A1 | 8/2009 | Saito et al. | |
| 2011/0082909 | A1 | 4/2011 | Ishibashi | |
| 2015/0145979 | A1 | 5/2015 | Tashiro et al. | |

FOREIGN PATENT DOCUMENTS

| JP | 2006-043238 A | 2/2006 |
| JP | 2007-111358 A | 5/2007 |
| JP | 2012-248031 A | 12/2012 |
| JP | 2014-147464 A | 8/2014 |
| WO | 2007/129482 A1 | 11/2007 |
| WO | 2014/181679 A1 | 11/2014 |
| WO | 2014/192689 A1 | 12/2014 |

OTHER PUBLICATIONS

May 1, 2018 Office Action issued in Japanese Patent Application No. 2017-075192.
Aug. 14, 2018 Extended European Search Report issued in European Patent Application No. 15873209.9.
Mar. 29, 2016 Search Report issued in International Patent Application No. PCT/JP2015/086094.
Nov. 1, 2016 Office Action issued in Japanese Patent Application No. 2016-546121.
Mar. 29, 2016 Written Opinion issued in International Patent Application No. PCT/JP2015/086094.
Mar. 7, 2017 Decision to Grant issued in Japanese Patent Application No. 2016-546121.
Jan. 28, 2019 Office Action issued in Chinese Patent Application No. 201580070092.1.
Dec. 4, 2018 Notification of Reasons for Refusal issued in Japanese Patent Application No. 2017-075192.

\* cited by examiner

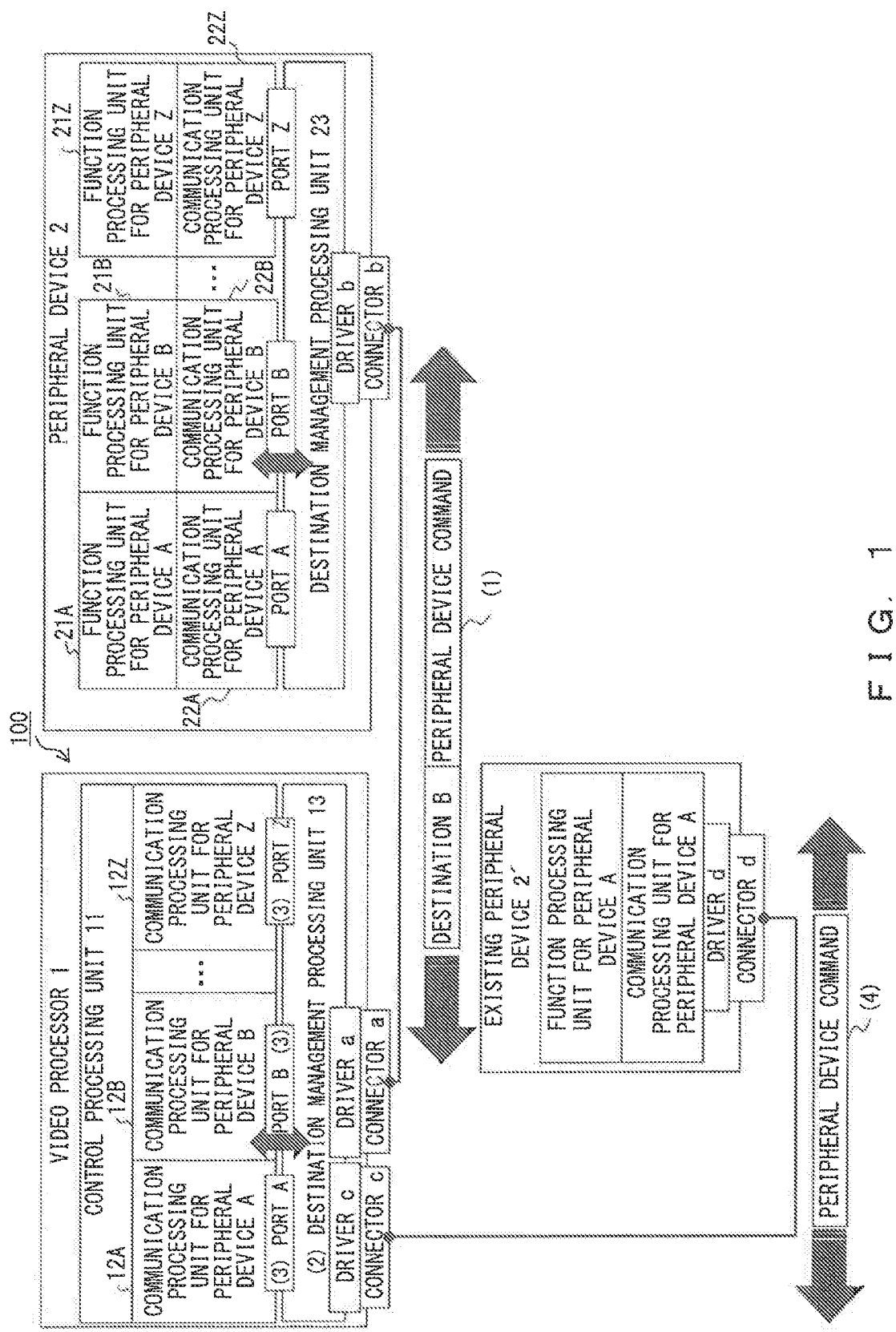
F I G. 1

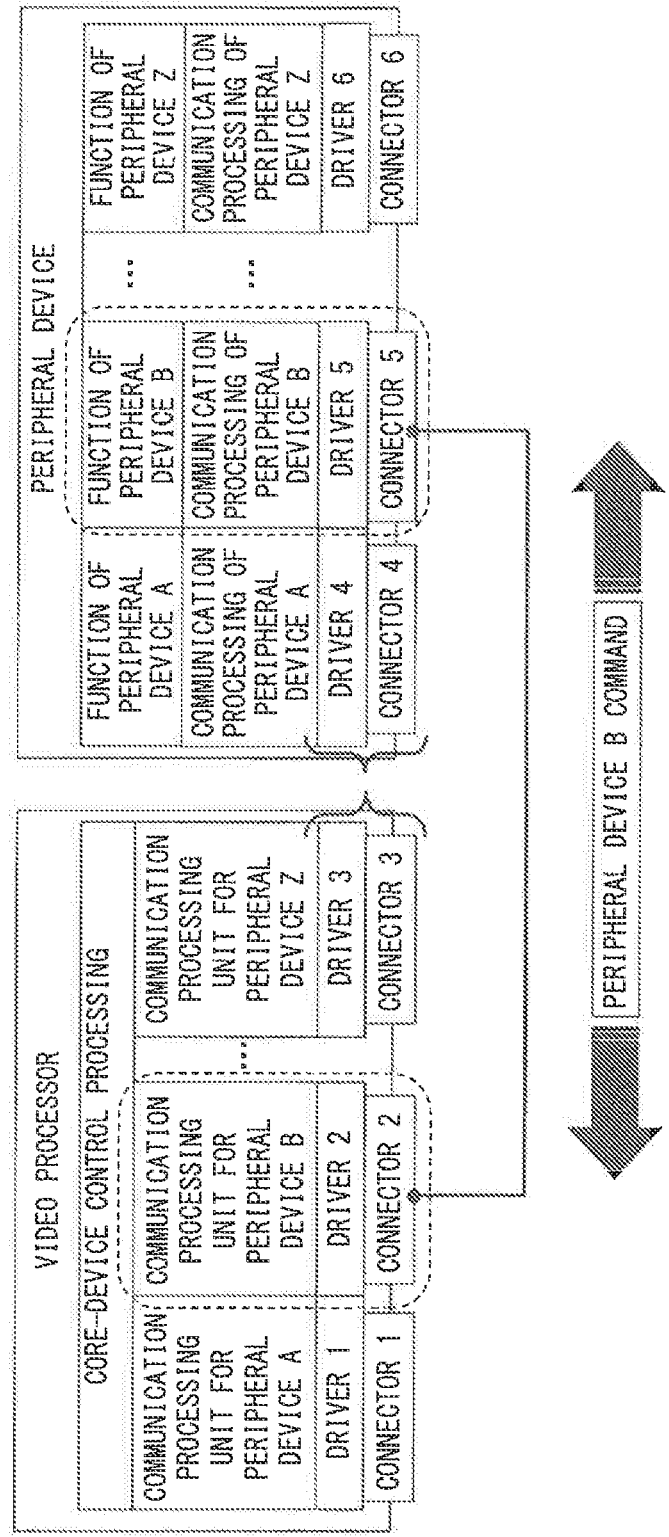
F I G. 2A

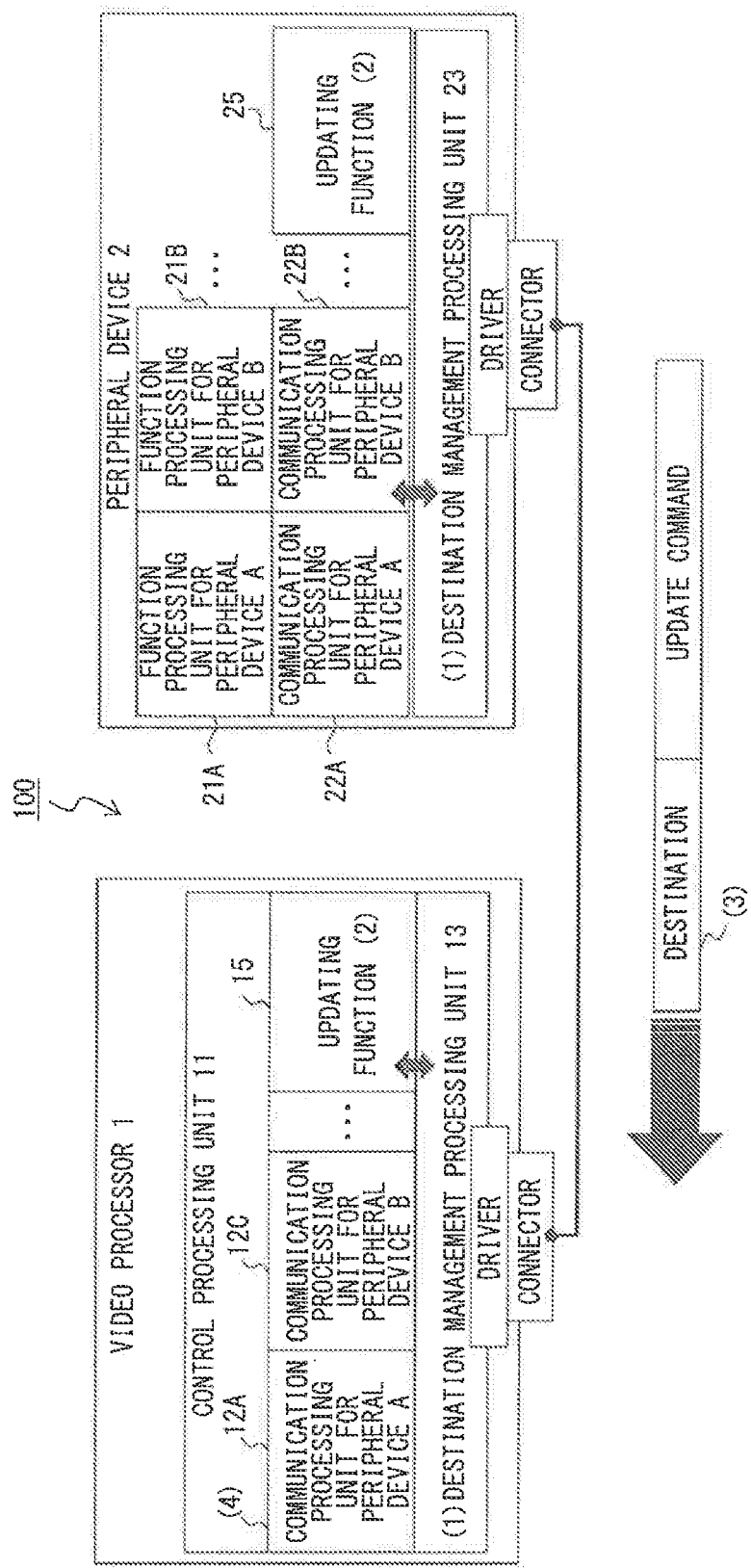
F I G. 5

ENDOSCOPIC SYSTEM

CROSS-REFERENCE TO RELATED APPLICATIONS

This application is based upon and claims the benefit of priority of the prior Japanese Patent Application No. 2014-263961, filed Dec. 26, 2014, the entire contents of which are incorporated herein by reference.

This is a Continuation Application of PCT Application No. PCT/JP2015/086094, filed Dec. 24, 2015, which was not published under PCT Article 21(2) in English.

FIELD

The present invention relates to an endoscopic system and more specifically to an endoscopic system including an endoscopic video processor and a peripheral device that communicates with the endoscopic video processor and is used along with the endoscopic video processor.

BACKGROUND

As disclosed in Japanese Laid-open Patent Publication No. 2007-111358, in an endoscopic system, an endoscopic video processor (hereinafter referred to as a processor) that performs, for example, processing on an endoscope image is connected to another device through a network and performs specified processing according to a command issued by the another device. The processor and other devices such as a peripheral device perform transmission and reception of a command between them using a specified protocol.

As disclosed in Japanese Laid-open Patent Publication No. 11-4238, not only in an endoscopic system but also in a commonly used communication system in which a plurality of devices are connected to one another through a network, a device that has received data determines the destination of the data using information added to the data. When the data is to be destined for the device itself, the device retrieves the data, and when the data is to be destined for another device, the device performs a transfer of the data.

In general, endoscopic video processors have a life cycle longer than peripheral devices, and the time period from the release of a certain model of an endoscopic video processor to the release of its successor model is long. On the other hand, peripheral devices have a relatively shorter life cycle. Thus, when a higher-performance successor model of a peripheral device is released, it is relatively often the case that the successor model is connected to an endoscopic video processor instead of its existing model.

However, a newly released peripheral device may use a communication protocol different from that of its existing model.

SUMMARY

A video processor according to an aspect of the present invention includes: a plurality of communication processing units that include at least one communication processing unit that performs processing that corresponds to an input command; and a destination management processing unit to which a command including information that indicates a destination is input from a peripheral device that has a specified function, wherein when the destination indicated by the information included in the input command is one of the plurality of communication processing units, the destination management processing unit outputs the command to the one of the plurality of communication processing units which corresponds to the destination, and when the destination indicated by the information included in the input command is not any of the plurality of communication processing units, the destination management processing unit outputs the command to a specified communication processing unit from among the plurality of communication processing units.

BRIEF DESCRIPTION OF DRAWINGS

The present invention will be more apparent from the following detailed description when the accompanying drawings are referenced.

FIG. 1 illustrates a method for introducing a peripheral device into an endoscopic system according to a first embodiment;

FIGS. 2A and 2B illustrate conventional methods for connecting a video processor to the peripheral device;

FIG. 5 illustrates a method for updating the video processor in an endoscopic system according to a third embodiment.

DESCRIPTION OF EMBODIMENTS

Figure 2B:
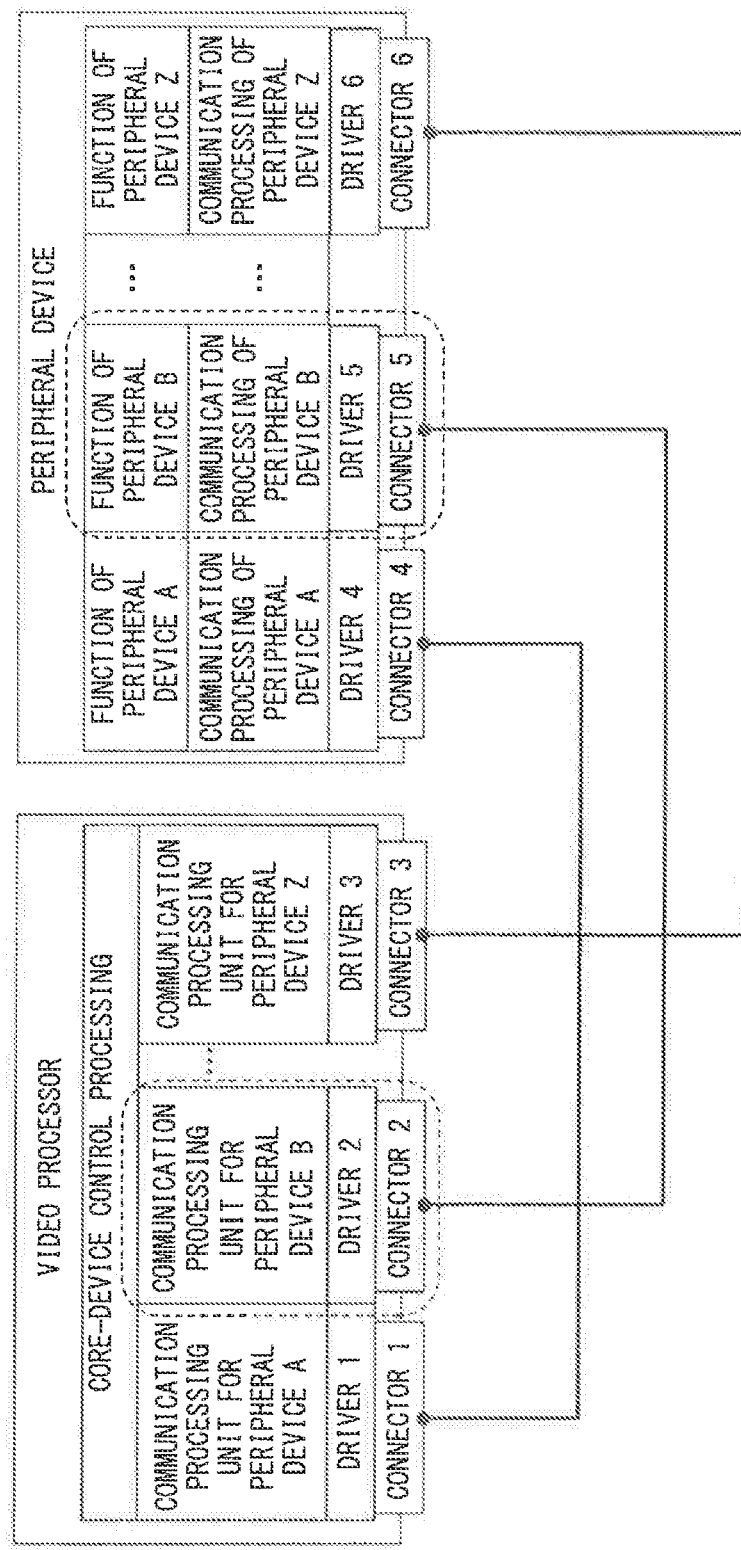

Embodiments of the present invention will now be described with reference to the drawings.

First Embodiment

FIG. 1 illustrates a method for introducing a peripheral device into an endoscopic system according to the present embodiment. An endoscopic system 100 illustrated in FIG. 1 includes an endoscopic video processor (hereinafter referred to as a video processor) 1 and a peripheral device 2, wherein the video processor 1 and the peripheral device 2 are connected to each other through their respective communication connectors.

The peripheral device 2 includes function processing units 21A to 21Z that respectively correspond to peripheral devices A to Z, communication processing units 22A to 22Z that respectively correspond to the peripheral devices A to Z, and a destination management processing unit 23. The peripheral device 2 is used along with the video processor 1 and a scope (not illustrated in FIG. 1) when an operator performs, for example, an examination or an operation using the endoscopic system 100, and realizes various functions provided by the peripheral devices A to Z. The peripheral device 2 of FIG. 1 has a configuration in which functions of a plurality of types of peripheral devices (the peripheral devices A, B, . . . , and Z) are included in one device. Each of the peripheral devices A to Z is configured by a function processing unit 21 that performs processing with respect to a respective function and a communication processing unit 22 that performs communication processing needed to implement the function.

The video processor 1 includes a control processing unit 11, communication processing units for the respective peripheral devices A to Z (12A to 12Z), and a destination management processing unit 13. The video processor 1 processes an imaging signal obtained by performing imagecapturing using the scope (not illustrated in FIG. 1), so as to generate an image signal. Further, the video processor 1 realizes the functions of the peripheral devices A to Z by performing specified processing such as a control of an endoscopic device according to commands from the peripheral devices A to Z of the peripheral device 2.

The video processor 1 includes the destination management processing unit 13 between the communication processing units 12 and a communication driver a, and the peripheral device 2 includes the destination management processing unit 23 between the communication processing units 22 and a communication driver b. The destination management processing unit 13,23 is a communication module that performs destination management processing on a command. When the destination management processing unit 13,23 receives, from the communication processing unit 12,22 situated above the destination management processing unit 13,23, a command to be transmitted to its counterpart's device, the destination management processing unit 13,23 performs processing of adding, to the command, information that indicates a destination. Further, when the destination management processing unit 13,23 receives the command from the communication processing unit 22,12 included in its counterpart's device, the destination management processing unit 13,23 refers to the information that indicates a destination and is added to the command, and performs processing of transferring the command to a corresponding one of the communication processing units 12,22 for the peripheral devices A to Z in its device through a corresponding port from among the ports A to Z.

The following are specific descriptions of how to cause the video processor 1 and the peripheral device 2 to cooperate with each other so as to realize the functions of the peripheral devices A to Z in the endoscopic system 100 according to the present embodiment. Here, an example of realizing the function of the peripheral device B from among a plurality of functions (the functions of the peripheral devices A to Z) of the peripheral device 2 is described.

First, the function processing unit 21B of the peripheral device 2 performs processing needed to realize the function of the peripheral device B in the endoscopic system 100. When a command is to be transmitted to the video processor 1 upon implementing the function of the peripheral device B, the function processing unit 21B reports it to the communication processing unit 22B. The communication processing unit 22B generates a necessary command and provides the generated command to the destination management processing unit 23 through the port B.

The ports A to Z are respectively provided by the destination management processing unit 23 to the communication processing units 22A to 22Z that are situated above the destination management processing unit 23 and arranged to respectively identify the communication processing units 22A to 22Z.

When the destination management processing unit 23 receives a command from the communication processing unit 22B, the destination management processing unit 23 performs destination management processing on the command. Specifically, the destination management processing unit 23 adds, to a specified position in the command such as a specified field in a header, information that indicates that the command is to be destined for the peripheral device B. Then, the destination management processing unit 23 transmits, to the video processor 1 and through the driver b and a connector b, the command to which the information that indicates a destination has been added (see (1) in FIG. 1).

When the destination management processing unit 13 of the video processor 1 receives the command through a connector a and the driver a, the destination management processing unit 13 of the video processor 1 performs destination management processing on the command. Specifically, the destination management processing unit 13 determines the information that indicates a destination and is added to the specified position of the received command, and distributes the command to a specified communication processing unit 12 from among the communication processing units 12A to 12Z. In the example of FIG. 1, the information that indicates that the command is to be destined for the peripheral device B is added. Thus, the destination management processing unit 13 transfers the command to the communication processing unit 12B through the port B (see (2) in FIG. 1).

The communication processing unit 12B receives the command through the port B (see (3) in FIG. 1). The communication processing unit 12B performs processing needed according to the received command.

The control processing unit 11 controls each component that configures the video processor 1. In this case, the control processing unit 11 controls the destination management processing unit 13 performing processing of transmitting/receiving a command from/to the peripheral device 2 and controls processing of causing each component to perform specified processing according to the command received from the peripheral device 2 by the communication processing unit 12B. Accordingly, processing needed to implement the function of the peripheral device B is performed in the video processor 1.

The example of transmitting a command from the peripheral device 2 to the video processor 1 has been described with reference to FIG. 1, but also in the case in which a command is transmitted from the video processor 1 to the peripheral device 2, similar processing is performed in the destination management processing unit 13 on the transmission side and in the destination management processing unit 23 on the reception side.

As described above, in the endoscopic system 100 according to the present embodiment, when the communication processing unit 12(12A-12Z),22(22A-22Z) included in each of the video processor 1 and the peripheral device 2 transmits a command between the video processor 1 and the peripheral device 2 in order to implement the function of a corresponding peripheral device from among the peripheral devices A to Z, the destination management processing unit 13,23 adds, to the command, information that indicates a destination, and transmits the command to its counterpart's device. When the destination management processing unit 13,23 receives the command from its counterpart's device, the destination management processing unit 13,23 determines the information that indicates a destination and is added to the command, and transfers the command to a specified communication processing unit 12 from among the communication processing units 12A-12Z,22A-22Z.

A conventional endoscopic system has been limited to, for example, being needed to implement the same protocol in the peripheral device 2 and the video processor 1. Thus, conventionally, as illustrated in FIG. 2A, a driver and a connector are needed to be connected to a corresponding driver and a corresponding connector between the devices according to a used function (peripheral devices A to Z), or as illustrated in FIG. 2B, all drivers and connectors are needed to be respectively connected to corresponding drivers and connectors in advance. In the configuration of FIG. 2A, even if a plurality of functions A to Z are implemented in the peripheral device, it will be possible to only use a portion of the functions. In the configuration of FIG. 2B, wiring will be complex because there is a need to establish a physical connection for each of the peripheral devices A to Z.

On the other hand, as illustrated in FIG. 1, in the endoscopic system 100 according to the present embodiment, the destination management processing unit 13,23 included in each of the video processor 1 and the peripheral device 2 adds, to a command, information that indicates which of the peripheral devices A to Z the command is to be destined for, and transfers the command to a specified communication processing unit 12,22 included in each of the video processor 1 and the peripheral device 2. In the video processor 1 or the peripheral device 2 that has received the command, the destination management processing unit 13,23 determines which of the peripheral devices A to Z the command is destined for, and distributes the command to a corresponding communication processing unit 12,22. This results in being able to perform a communication between the video processor 1 and the peripheral device 2 without taking into consideration a connector, that is, a physical connection.

An existing model may be modified with respect to the functions of the peripheral devices A to Z (such as the function processing unit 21 and the communication processing unit 22) included in a newly released peripheral device 2. In the example described above, it is assumed that the existing model has been modified with respect to the function of the peripheral device B (such as the function processing unit 21 and the communication processing units 22) included in the newly released peripheral device 2. According to the endoscopic system 100 of the present embodiment, there will be no need to perform processing of, for example, updating the video processor 1 in order to keep up with the modification even in the above-described case. This makes it possible to introduce a newly released peripheral device 2 into the endoscopic system 100 by an easy method so as to cause the video processor 1 and the newly released peripheral device 2 to cooperate with each other.

Further, the endoscopic system 100 according to the present embodiment permits the video processor 1 to communicate with an existing peripheral device as well.

An existing peripheral device 2' illustrated in FIG. 1 is connected to the connector c of the video processor 1 through a connector d. The existing peripheral device 2' does not include the destination management processing unit 23. Thus, the existing peripheral device 2' does not perform destination management processing, and transmits, to the video processor 1, a command to which information that indicates a destination is not added (see (4) in FIG. 1). However, in the present embodiment, even when the video processor 1 has received a command on which destination management processing has not been performed, the video processor 1 determines an appropriate destination and transfers the command to a specified communication processing unit 12.

Specifically, when the destination management processing unit 13 of the video processor 1 has determined, as a result of referring to the command, that information that indicates a destination is not added, the destination management processing unit 13 further refers to information that indicates which of the communication connectors the command has been received through. The destination management processing unit 13 holds, in a storage (not illustrated in FIG. 1) and for each of the connected peripheral devices 2 and 2' connected to the video processor 1, information on which of the communication connectors the peripheral device is connected through and information on which of the peripheral devices A to Z is included. In the example of FIG. 1, the command has been received through the connector c, so the destination management processing unit 13 determines that the communication processing unit 12 which corresponds to the connector c is the "communication processing unit 12A for the peripheral device A". Accordingly, the destination management processing unit 13 transfers the command received from the existing peripheral device 2' to the communication processing unit 12A through the port A.

As described above, the endoscopic system 100 according to the present embodiment permits the video processor 1 to communicate not only with the newly released peripheral device but also with the existing peripheral device 2'. The peripheral device 2 has a life cycle shorter than that of the video processor 1, so a function that the existing peripheral device does not have may be added to the newly released peripheral device 2. Even when a new function has been added, there will be no need to communicate with the video processor 1 through a connector that corresponds to the new function if destination management processing on a command is performed. In other words, the destination management processing unit 13 determines which of the communication processing units 12 a command is destined for and transfers the command to the destination communication processing unit 12 through a port corresponding to the destination communication unit 12, so there is no need to take into consideration a connector or a driver. Further, with respect to a command transmitted from the existing peripheral device 2', the destination management processing unit 13 can also determine a corresponding communication processing unit 12 and transfer the command to the corresponding communication processing unit 12. This results in being able to easily introduce the newly released peripheral device 2 into the endoscopic system 100 while maintaining the compatibility with the existing peripheral device 2'.

Further, a destination management device is implemented in each of the video processor 1 and the peripheral device 2, so the communication processing unit 12,22 that is situated above the destination management device does not have to take into consideration a physical connector. This also provides the advantage of being able to introduce various communication devices (communication standards) into a system.

Second Embodiment

The first embodiment described above relates to the method for introducing the newly released peripheral device 2 into the endoscopic system 100 when the existing model has been modified with respect to a function of a peripheral device n (such as a function processing unit 21n and a communication processing unit 22n) included in the newly released peripheral device 2. On the other hand, the present embodiment relates to a method for introducing the newly released peripheral device 2 into the endoscopic system 100 when a peripheral device n included in the newly released peripheral device 2 is a completely new device and the video processor 1 does not include a communication processing unit that corresponds to a function of the peripheral device n.

An endoscopic system according to the present embodiment is described below, focusing on the difference from the embodiment described above.

Figure 3:
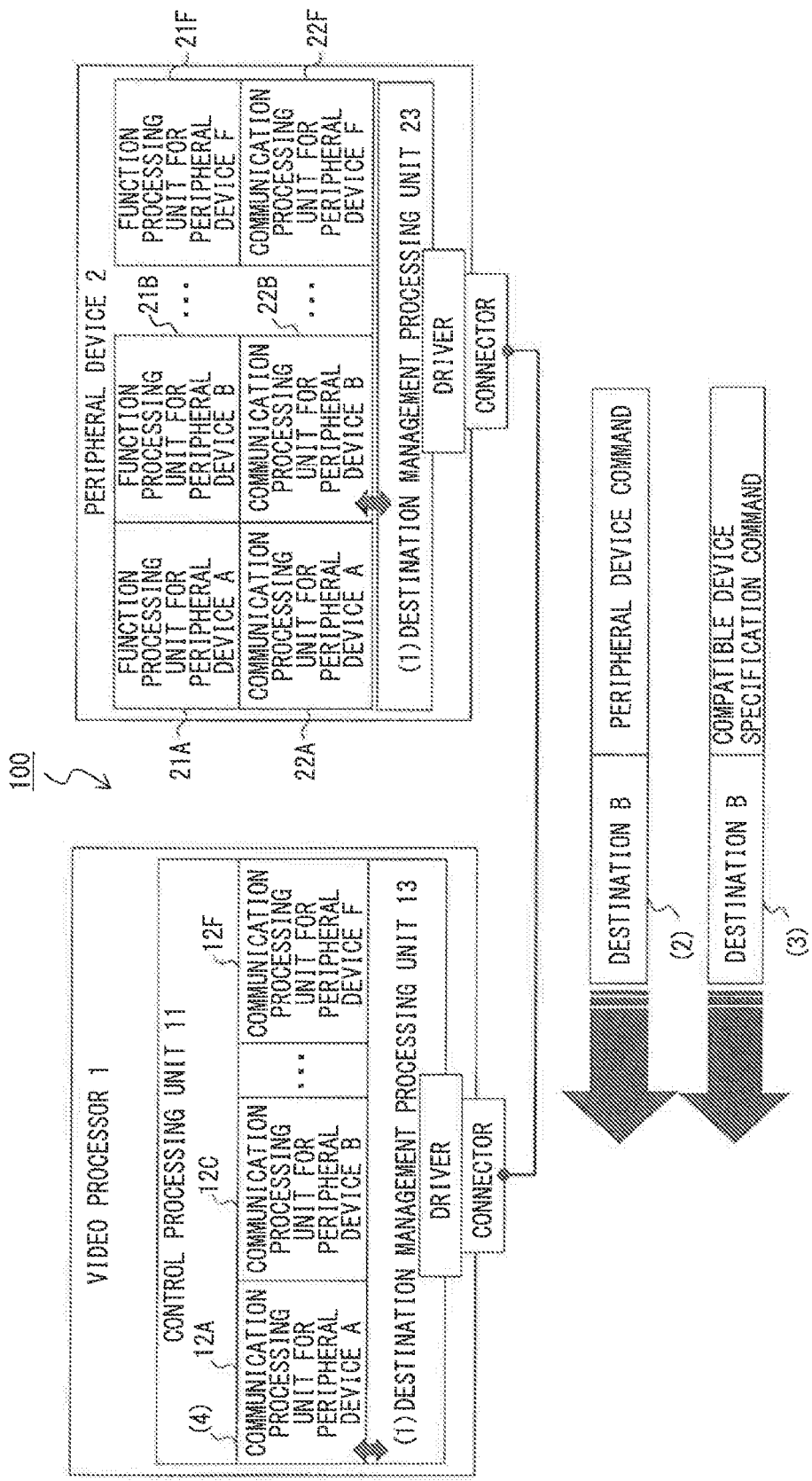
FIG. 3 illustrates a method for introducing the peripheral device into an endoscopic system according to a second embodiment.

FIG. 3 illustrates a method for introducing the peripheral device 2 into the endoscopic system according to the present embodiment. The operation of each component that configures the video processor 1 and the peripheral device 2 is similar to that in the embodiment described above, and the destination management processing unit 13,23 performs destination management processing, as in the embodiment described above. In other words, with respect to a command to be transmitted, the destination management processing unit 13,23 adds, to a specified position of the command, information that indicates a destination, and with respect to a received command, the destination management processing unit 13,23 refers to the information that indicates a destination so as to distribute the command to a specified communication processing unit.

In this case, the function of the peripheral device B has been added to the newly released peripheral device 2, wherein the newly released peripheral device 2 includes the function processing unit 21B and the communication processing unit 22B. On the other hand, the video processor 1 does not include the corresponding communication processing unit 12B. As an example, a method for implementing a function of a new peripheral device B in this system environment is described, the method including causing the video processor 1 to cooperate with the peripheral device 2 that includes the new peripheral device B.

First, the video processor 1 and the peripheral device 2 each obtain information on their counterpart when they are connected to each other. The information obtained here includes the configuration of the communication processing units 12,22 that are included in the counterpart, that is, the video processor 1 or the peripheral device 2. In the example of FIG. 3, information that indicates that the communication processing units 12 of the video processor 1 are the communication processing units 12A, 12C, . . . , and 12F for the peripheral devices A, C, . . . , and F, and information that indicates that the communication processing units 22 of the peripheral device are the communication processing units 22A, 22B, . . . , and 22F for the peripheral devices A, C, . . . , and F respectively correspond to the configuration of the communication processing units 12 and the configuration of the communication processing units 22.

As a result of comparing the information obtained from the peripheral device 2 with the information on the video processor 1, the destination management processing unit 13 of the video processor 1 recognizes that the peripheral device 2 includes the "communication processing unit 22B for the peripheral device B" but the video processor 1 does not include a corresponding communication processing unit. Thus, the destination management processing unit 13 determines that the video processor 1 is to be tentatively connected to the peripheral device 2 while regarding the peripheral device B of the peripheral device 2 as a "device in a similar category to the peripheral device A" (see (1) in FIG. 3). The destination management processing unit 13 holds, in the storage, information that indicates that the peripheral device B is to be dealt with as a device in a similar category to the peripheral device A.

Here, "a peripheral device n is to be dealt with as a device in a similar category to a peripheral device m" indicates that a command destined for the peripheral device n is to be distributed to a communication processing unit 12*m* of the peripheral device m.

After that, as a result of determining a destination of a command received from the peripheral device 2, when the destination has been determined to be the peripheral device B that is "a device in a similar category to the peripheral device A", the destination management processing unit 13 of the video processor 1 transfers the command to the communication processing units 12A of the peripheral device A (see (2) in FIG. 3). As described above, the communication processing unit 11A of the video processor 1 and the communication processing unit 22B of the peripheral device 2 tentatively perform processing of communicating with each other, which permits the video processor 1 and the peripheral device 2 to tentatively cooperate with each other to realize the function of the peripheral device B.

As in the first embodiment described above, the destination management processing unit 13 also transfers a command to the communication processing unit 12A through the port A in the present embodiment, although this is not illustrated in FIG. 3. The same applies to the descriptions of an embodiment described later.

In order to cause the video processor 1 and the peripheral device 2 to formally cooperate with each other to realize the function of the peripheral device B, the function processing unit 21B for the peripheral device B in the peripheral device 2 transmits a "compatible device specification command" to the video processor 1 (see (3) in FIG. 3). The compatible device specification command destined for the peripheral device B is a command that makes a request to recognize the peripheral device B as a peripheral device that can be dealt with and to deal with it.

The destination management processing unit 13 of the video processor 1 recognizes, from the information held in the storage and the received compatible device specification command, that the received compatible device specification command is to be destined for the "peripheral device B" tentatively dealt with in the video processor 1 as a device in a similar category to the peripheral device A. Then, the destination management processing unit 13 determines that the peripheral device B is to be associated with (the communication processing unit 12A for) the peripheral device A in the video processor 1 and a command is to be formally distributed to the communication processing unit 12A when the destination management processing unit 13 performs subsequent communications with the peripheral device B of the peripheral device 2 (see (4) in FIG. 3).

In the method illustrated in FIG. 3, when the peripheral device 2 includes a peripheral device n that is not included in the video processor 1, one of the communication processing units included in the video processor 1 is tentatively connected to the peripheral device n of the peripheral device 2, which permits the video processor 1 to cooperate with the peripheral device 2. However, in the endoscopic system 100 according to the present embodiment, the video processor 1 and the peripheral device 2 may be caused to tentatively cooperate with each other by a method other than the method illustrated in FIG. 3. This is specifically described with reference to FIG. 4.

Figure 4:
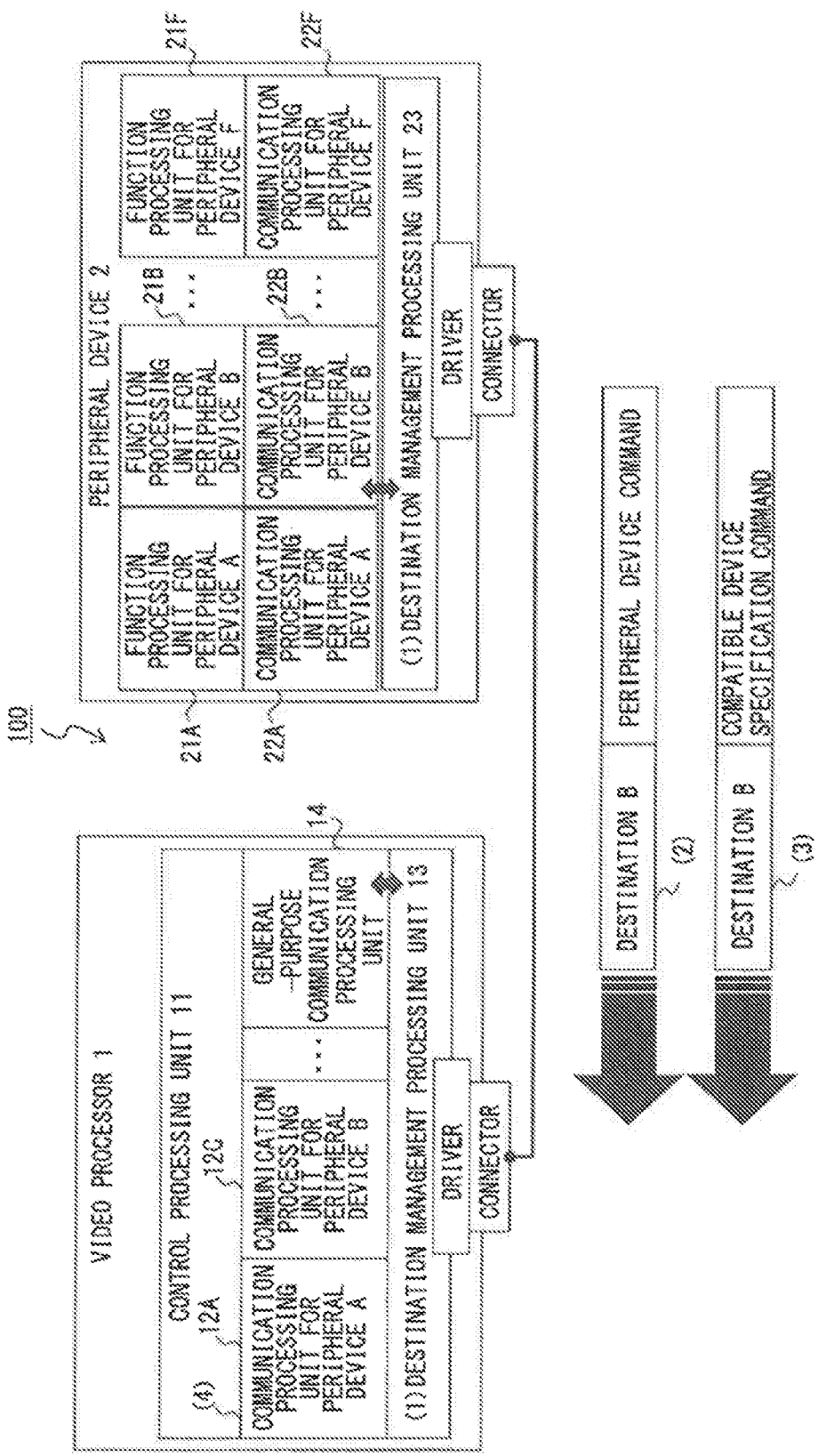
FIG. 4 illustrates another method for introducing the peripheral device into the endoscopic system according to the second embodiment.

FIG. 4 illustrates another method for introducing the peripheral device 2 into the endoscopic system 100 according to the present embodiment.

The video processor 1 illustrated in FIG. 4 is similar to that of FIG. 3 in that it does not include the corresponding communication processing unit 12B for the peripheral device B. On the other hand, the configuration of the video processor 1 of FIG. 4 is different from that of FIG. 3 in that it includes a general-purpose communication processing unit 14 that is able to perform communication processing regardless of the functions of the peripheral devices A, B, . . . .

When the video processor 1 and the peripheral device 2 are connected to each other, the video processor 1 and the peripheral device 2 each obtain information on their counterpart as in the above example described with reference to FIG. 3, and the obtained information is also similar to that in the above example described with reference to FIG. 3. However, in this case, the destination management processing unit 13 of the video processor 1 operates differently when it recognizes, as a result of comparing the information obtained from the peripheral device 2 with the information on the video processor 1, that the video processor 1 does not include a communication processing unit corresponding to the "communication processing unit 22B for peripheral device B" included in the peripheral device 2. In the configuration illustrated in FIG. 4, the destination management processing unit 13 assigns communication processing with respect to the peripheral device B to the general-purpose communication processing unit 14 and holds information on that in the storage (see (1) in FIG. 4).

After that, the destination management processing unit 13 of the video processor 1 distributes a command destined for the peripheral device B to the general-purpose communication processing unit 14 (see (2) in FIG. 4). This causes the video processor 1 and the peripheral device 2 to tentatively cooperate with each other.

Subsequent processing of causing the video processor 1 and the peripheral device 2 to formally cooperate with each other to realize the function of the peripheral device B is similar to the processing performed by the method of FIG. 3. However, with respect to a compatible device specification command that is transmitted and received here, not only is information that indicates the peripheral device B as a destination added to a specified position of the command, but also the command includes a request that "the destination peripheral device B be to be dealt with as the general-purpose communication processing unit 14 in the video processor 1" (see (3) in FIG. 4).

On the basis of the compatible device specification command received from the peripheral device 2, the destination management processing unit 13 of the video processor 1 determines that the peripheral device B is to be associated with the general-purpose communication processing unit 14 in the video processor 1. Then, the destination management processing unit 13 determines that a command is to be distributed to the general-purpose communication processing unit 14 when the destination management processing unit 13 performs subsequent communications with the peripheral device B of the peripheral device 2 (see (4) in FIG. 4).

As described above, the endoscopic system 100 according to the present embodiment makes it possible to perform destination management processing on a command transmitted and received between the video processor 1 and the newly released peripheral device 2 so as to cause the video processor 1 and the peripheral device 2 to properly cooperate with each other, even when the peripheral device 2 is provided with (a peripheral device that has) a completely new function.

Third Embodiment

In the first and second embodiments described above, destination management processing permits the video processor 1 to communicate with the peripheral device 2 without performing updating in the video processor 1, wherein the peripheral device 2 has been newly released with a configuration of the video processor 1 and a corresponding function has been added to the peripheral device 2. On the other hand, in the present embodiment, the video processor 1 is updated by an easy method, which permits a corporation with the peripheral device 2 to which a function of a peripheral device n (a function processing unit 21n and a communication processing unit 22n) has been added.

An endoscopic system according to the present embodiment is specifically described below.

FIG. 5 illustrates a method for updating the video processor in the endoscopic system according to the present embodiment. In the present embodiment, the destination management processing unit 13,23 performs destination management processing, wherein the destination management processing unit 13,23 adds, to a command to be transmitted, information that indicates a destination, and refers to the information that indicates a destination of a received command so as to distribute the received command, as in the first and second embodiments described above.

As illustrated in FIG. 5, in the endoscopic system 100 according to the present embodiment, the video processor 1 and the peripheral device 2 respectively include an updating function 15 and an updating function 25. The updating function 25 of the peripheral device 2 holds update data that is used when the video processor 1 communicates with the newly released peripheral device 2 and performs processing corresponding to, for example, a newly added function. When the updating function 15 of the video processor 1 has receives, from the peripheral device 2, a command that makes a request to perform updating and update data, the updating function 15 updates the video processor 1 according to this request. The updating functions 15 and 25 are respectively situated above the destination management processing units 13 and 23, and each transmit/receive a command to/from their counterpart's device (the newly released peripheral device 2 and the video processor 1, respectively) through an assigned port.

Referring to FIG. 5, how to perform a necessary updating of the video processor 1 so as to cause the video processor 1 and the peripheral device 2 to cooperate with each other in the endoscopic system 100 according to the present embodiment is specifically described.

Also in the present embodiment, the video processor 1 and the peripheral device 2 respectively include the destination management processing units 13 and 23 as described above, and perform destination management processing similar to that in the embodiments described above. A command on which destination management processing has been performed is transmitted and received between the video processor 1 and the peripheral device 2, which permits the video processor 1 and the peripheral device 2 to perform transmission and reception of a command without taking into consideration a communication driver or a connector. Destination management processing is also performed on a command with respect to an updating of the video processor 1 (see (1) in FIG. 5).

Specifically, first, the updating function 25 of the peripheral device 2 refers to data that the updating function 25 holds so as to determine whether updating is to be performed. Update data of a video processor's version suitable for a connection to the peripheral device 2 is stored in a storage (not illustrated in FIG. 5) of the updating function 25 for each type of processor. The updating function 25 communicates with the updating function 15 of the video processor 1 so as to obtain a version of the video processor 1 (see (2) in FIG. 5). Then, on the basis of the obtained version and a version that corresponds to a type of the video processor 1 in FIG. 5 from among the held pieces of update data, the updating function 25 determines whether the video processor 1 is to be updated.

When the updating function 25 has determined that it is possible to perform an updating of the video processor 1 and that the updating is to be performed. The updating function 25 transmits, to the video processor 1, an update command that makes a request to update the video processor 1 and data needed for the updating (see (3) in FIG. 5). Information that indicates the "updating function 15" is set to be a destination of the update command.

When the updating function 15 of the video processor 1 receives the update command and the data needed for the updating from the peripheral device 2, the updating function 15 performs the updating using the command and the data. After the updating processing is terminated, the video processor 1 is restarted and processing of connecting the video processor 1 to the peripheral device 2 is performed. This permits the video processor 1 and the newly released peripheral device 2 to cooperate with each other.

As described above, in the endoscopic system 100 according to the present embodiment, update data of a version suitable for each type of video processor 1 is stored in the newly released peripheral device 2. The updating function 25 of the peripheral device 2 obtains a current version of the video processor 1 so as to determine whether an updating is to be performed. When the updating has been determined to be performed in order to cause the video processor 1 and the peripheral device 2 to cooperate with each other, the peripheral device 2 transmits, to the video processor 1, a command that makes a request to perform the updating and data needed for the updating. When the command that makes a request to perform the updating and the data needed for the updating have been transmitted from the peripheral device 2, the updating function 15 of the video processor 1 performs the updating. This results in there being no need for someone such as a support engineer to go to the site to perform updating every time the updating is needed to be performed, which makes it possible to cause the video processor 1 and the peripheral device 2 to easily cooperate with each other.

Further, update data of a version suitable for each type of video processor 1 is stored in the peripheral device 2 and an updating is performed using this data, which results in determining a version of the video processor 1 for each product. As a result, a connection to the video processor 1 or the like is likely to be easily secured. In addition, it is possible to avoid being unable to establish a connection due to a difference in version. It is also possible to appropriately implement a function corresponding to the newly released peripheral device 2 in the video processor 1. This results in being able to avoid an improper restriction on an implementable function as much as possible except for the cases of a restriction due to hardware configurations of devices (the video processor 1 and the newly released peripheral device 2) that configure the endoscopic system 100.

The present invention is not limited to the embodiments described above and may be embodied by modifying the constituent elements without departing from the scope of the invention. Various embodiments of the present invention may be formed with any appropriate combination of a plurality of constituent elements disclosed in the embodiments described above. For example, all of the constituent elements disclosed in the embodiments may be combined appropriately. Further, constituent elements may be appropriately combined in different embodiments. It should be understood that various modifications and applications can be made without departing from the spirit of the invention.

What is claimed is:

1. A video processor comprising:
a plurality of communication processing units that include at least one communication processing unit that performs processing that corresponds to an input command; and
a destination management processing unit to which a command including information that indicates a destination is input from a peripheral device that has a specified function, wherein when the destination indicated by the information included in the input command is one of the plurality of communication processing units, the destination management processing unit outputs the command to the one of the plurality of communication processing units which corresponds to the destination, and when the destination indicated by the information included in the input command is not any of the plurality of communication processing units, the destination management processing unit outputs the command to a specified communication processing unit from among the plurality of communication processing units, and the destination management processing unit determines based on the input information a communication connector for selecting the specified communication processing unit, the input information including a communication connector origin and a corresponding peripheral device, wherein:
the plurality of communication processing units include a general-purpose communication processing unit that can communicate with the peripheral device regardless of a function of the peripheral device, and
the specified communication processing unit is the general-purpose communication processing unit.

2. The video processor according to claim 1, wherein
when a command that makes a request that the specified communication processing unit perform processing on the command output to the specified communication processing unit is input from the peripheral device, the specified communication processing unit formally performs the processing.

3. A video processor according to claim 1, further comprising:
an updating function unit that updates the video processor, wherein
when the destination management processing unit further receives, from the peripheral device, a command that makes a request to perform updating and update data, the destination management processing unit outputs the command and the update data to the updating function unit, and
the updating function unit performs the updating of the video processor using the command that makes a request to perform updating and the update data.

4. A video processor comprising:
a plurality of communication processing units that include at least one communication processing unit that performs processing that corresponds to an input command; and
a destination management processing unit to which a command including information indicating a destination is input from a peripheral device, and that outputs the command to a communication processing unit from among the plurality of communication processing units that corresponds to the destination, wherein
the plurality of communication processing units include a general-purpose communication processing unit that can communicate with the peripheral device regardless of a function of the peripheral device, and when the destination indicated by the information included in the input command is not any of the plurality of communication processing units, the destination management processing unit outputs the command to a specified communication processing unit from among the plurality of communication processing units, and the destination management processing unit determines based on the input information a communication connector for selecting the specified communication processing unit, the input information including a communication connector origin and a corresponding peripheral device.

* * * * *